US006566074B1

(12) United States Patent
Goetinck

(10) Patent No.: US 6,566,074 B1
(45) Date of Patent: May 20, 2003

(54) METHODS OF MODULATING CELL ATTACHMENT AND MIGRATION

(75) Inventor: Paul F. Goetinck, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/525,649

(22) Filed: Mar. 15, 2000

Related U.S. Application Data

(60) Provisional application No. 60/124,396, filed on Mar. 15, 1999.

(51) Int. Cl.[7] .......................... G01N 33/53; C12P 21/06; C12N 1/20
(52) U.S. Cl. ..................... 435/7.1; 435/252.3; 435/69.1; 435/69.7; 530/395
(58) Field of Search ....................... 530/395; 435/252.3, 435/69.1, 69.7, 7.1

(56) References Cited

U.S. PATENT DOCUMENTS 5,486,599 A    1/1996    Saunders et al.

OTHER PUBLICATIONS

Herter et al. The journal of biology chemistry vol. 269 No. 7, Jan. 7, pp. 696–703, 1994.*
Woods et al. Matrix Biology Journal of the international society for matrix biology vol. 17. No. n7 pp. 461–528 Nov. 1998.*
Baciu et al., "Molecular Cloning and Genomic Organization of Chicken Syndecan–4", *The Journal of Biological Chemistry*, vol. 269, No. 1, 696–703 (1994).
Baciu et al., "Protein Kinase C Regulates the Recruitment of Syndecan–4 into Focal Contacts", *Molecular Biology of the Cell*, vol. 6, 1503–1513 (1995).
Gallagher et al., Meeting Reports from Molecular Cell Biology of Cytokines and Matrix, (1994).
Gallo et al., "Syndecans, Cell Surface Heparan Sulfate Proteoglycans, are Induced by a Proline–Rich Antimicrobial Peptide from Wounds", *Proceedings of the National Academy of Sciences*, vol. 91, 11035–11039 (1994).
Gallo et al., "Syndecans–1 and –4 Are Induced During Wound Repair of Neonatal but Not Fetal Skin", *The Journal of Investigative Dermatology*, vol. 107 No. 5 (1996).
Horowitz et al., "Phosphorylation of the Cytoplasmic Tail of Syndecan–4 Regulates Activation of Protein Kinase Cα", *The Journal of Biological Chemistry*, vol. 273, No. 40, 25548–25551 (1998).
Horowitz et al., "Regulation of Syndecan–4 Phosphorylation in Vivo", *The Journal of Biological Chemistry*, vol. 273, No. 18, 10914–10918 (1998).
Kainulainen et al., "Syndecans, Heparan Sulfate Proteoglycans, Maintain the Proteolytic Balance of Acute Wound Fluids", *The Journal of Biological Chemistry*, vol. 273, No. 19, 11563–11569 (1998).

Lee et al., "Solution Structure of a Syndecan –4 Cytoplasmic Domain and Its Interaction with Phosphatidylinositol 4,5–Bisphospate", *The Journal of Biological Chemistry*, vol. 273, No. 21, 13022–13029 (1998).
Li et al., "Macrophage–Dependent Regulation of Syndecan Gene Expression", *Circulation Research*, vol. 81, No. 5, (1997).
Liu et al, "Heparan Sulfate Proteoglycans as Adhesive and anti–invasive Molecules", *The Journal of Biological Chemistry*, vol. 273, No. 35, 22825–22832 (1998).
McFall et al., "Characterization of the High Affinity Cell–binding domain in the Cell Surface Proteoglycan Syndecan–4", *The Journal of Biological Chemistry*, vol. 273, No. 43 28270–28276 (1998).
McFall et al., "Identification of an Adhesion Site within the Syndecan–4 Extracellular Protein Domain", *The Journal of Biology Chemistry*, vol. 272, No. 20 12901–12904, (1997).
Mertens, et al., "Heparan Sulfate Expression in Polarized Epithelial Cells: The Apical Sorting of Glypican (GPI–anchored Proteoglycan) Is Inversely Related to Its Heparan Sulfate Content", *The Journal of Cell Biology*, vol. 132, 487–497 (1996).
Nakanishi et al., "Switch of Coenzyme Specificity of Mouse Lung Carbonyl Reductase by Substitution of Threonine 38 with Aspartic Acid", *The Journal of Biological Chemistry*, vol. 272, No. 4 2218–2222 (1997).
Oh et al., "Multimerization of the Cytoplasmic Domain of Syndecan–4 is Required for Its Ability to Activate Protein Kinase C", *The Journal of Biological Chemistry*, vol. 272, No. 18, 11805–11811 (1997).
Oh et al., "Syndecan–4 Proteoglycan Regulates the Distribution and Activity of Protein Kinase C", *The Journal of Biological Chemistry*, vol. 272, No. 13, 8133–8136 (1997).

(List continued on next page.)

*Primary Examiner*—Remy Yucel
*Assistant Examiner*—Konstantina Katcheves
(74) *Attorney, Agent, or Firm*—Fish & Richardson PC

(57) ABSTRACT

The invention features a method of modulating, e.g., inhibiting or promoting, the spatial or positional relationship of a cell to a substrate, or modulating the intracellular response of a cell to a substrate, in vitro or in vivo. The method includes administering an agent which modulates the interaction, e.g., the binding, of the syndecan-4 ectodomain with a counterligand, thereby modulating the spatial or positional relationship of a cell to a substrate, or modulating the intracellular response of a cell to a substrate. The preferred counterligand is an ECM component, e.g., the heparin-binding domain of a component of the extracellular matrix (ECM) such as fibronectin, vitronectin, a laminin or a collagen. The invention also features methods of identifying compounds which modulate, e.g., inhibit or promote, the spatial or positional relationship of a cell to a substrate, or modulate the intracellular response of a cell to a substrate, and methods of treating a subject having a disorder characterized by unwanted or abnormal cell adhesion or spreading, e.g., cancer.

7 Claims, 2 Drawing Sheets-

OTHER PUBLICATIONS

Oh, et al., "Syndecan–4 Proteoglycan Cytoplasmic Domain and Phosphatidylinositil 4,5–Bisphospate Coordinately Regulate Protein Kinase C Activity", *The Journal of Biological Chemistry*, vol. 273, No. 17, 10624–10629, (1998).

Olsson et al., "Fatty Acids Modulate the Composition of Extracellular Matrix in Cultured Human Arterial Smooth Muscle Cells by Altering the Expression of Genes for Proteoglycan Core Proteins", *Journal of the American Diabetes Association*, vol. 48, 616–622 (1999).

Oritani et al., "Identificaiton of Stromal Cell Products That Interact with Pre–B Cells", *The Journal of Cell Biology*, vol. 134, No. 3, (1996).

Ott et al., "Tryosine Phosphorylation of Syndecan–1 and –4 Cytoplasmic Domains in Adherent B82 Fibroblasts", *The Journal of Biological Chemistry*, vol. 273, No. 52 35291–35298 (1998).

Penc et al., "Dermatan Sulfate Released after Injury Is a Potent Promoter of Fibroblast Growth Factor–2 Function", *The Journal of Biological Chemistry*, vol. 273, No. 43, 28116–28121 (1998).

Prasthofer et al., "Protein Kinase C Phosphorylates Two of the Four Known Syndecan Cytoplasmic Domains In Vitro", *Biochemistry and Molecular Biology International*, vol. 36, No. 4 793–802 (1995).

Pyke et al., "Proteoglycan Expression in the Normal Rat Kidney", *Nephron* 461–470 (1997).

Renard et al., "Infection of WHV/c–myc Transgenic Mice with Moloney Murine Leukaemia Virus and Proviral Insertion near the Syndecan–4 Gene in an Early Liver Tumour", *Institute Pasteur/Elsevier*, Paris (1998).

Roskams et al., "Heparan Sulphate Proteoglycan Expression in Human Primary Liver Tumours", *The Journal of Pathology*, vol. 185, No. 3 (1998).

Roskams et al., Haparan Sulfate Proteoglycan Expression in Chronic Cholestatic Human Liver Diseases, *Hepatology*, vol. 24, No. 3 524–532 (1996).

Saoncella et al., "Syndecan–4 Signals Cooperatively with Integrins in a Rhodependent Manner in the Assembly of Focal Adhesions and Actin Stress Fibers", Proc. Natl. Acad. Sci. USA, vol. 96, 2805–2810 (1999).

Setty et al., "Interactions of Type IV Collagen and Its Domains with Human Mesangial Cells", *The Journal of Cell Biological Chemistry*, vol. 273, No. 20, 12244–12249 (1998).

Smith et al., "Syndecan–4 Is a Primary–Response Gene Induced by Basic Fibroblast Growth Factor and Arterial Injury in Vascular Smooth Muscle Cells", *Arteriosclerosis, Thrombosis, and Vascular Biology*, vol. 17, No. 1, (1997.

Spring et al., "Mapping of the Syndecan Genes in the Mouse: Linkage with Members of the Myc Gene Family", *Genomics* 21, 597–601 (1994).

Stanley et al., "Heparan Sulfate–mediated Cell Aggregation", *The Journal of Biological Chemistry* vol. 270, No. 10, 5077–5083 (1995).

Steinfeld et al., "Stimulation of Fibroblast Growth Factor Receptor–1 Occupancy and Signaling by Cell Surface–associated Syndecans and Glypican", *The Journal of Cell Biology*, vol. 133, No. 2, 405–416 (1996).

Subramanian et al., "Regulated Shedding of Syndecan–1 and –4 Ectodomains by Thrombin and Growth Factor Receptor Activation", *The Journal of Biological Chemistry*, vol. 272, No. 23 14713–14720 (1997).

Uetsuki et al., "Structure and Expression of the Mouse Necdin Gene", *The Journal of Biological Chemistry*, vol. 271, No., 918–924 (1996).

Wong et al., "Syndecan–1 is Up–Regulated in Ras–transformed Intestinal Epithelial Cells", *British Journal of Cancer*, 890–896 (1998).

Woods et al., "Protein Kinase C Involvement in Focal Adhesion Formation", *Journal of Cell Science* vol. 101, 227–290 (1992).

Woods et al., "Syndecan 4 Heparan Sulfate Proteoglycan Is a Selectively Enriched and Widespread Focal Adhesion Component", *Molecular Biology of the Cell*, vol. 5, 813–192, (1994).

Woods et al., "Syndecan–4 Binding to the High Affinity Heparin–Binding Domain of Fibronectin Drives Focal Adhesion Formation Fibroblasts", *Archives of Biochemistry and Biophysics*, vol. 374, No. 1 66–72 (2000).

Woods, et al., "Syndecans: Synergistic Activators of Cell Adhesion", Trends in Cell Biology, p. 189 (1998).

Yeaman et al., "Membrane–Anchored Proteoglycans of Mouse Macrophages: P338D1 Cells Express a Syndecan–4–Like Heparan Sulfate Proteoglycan and a Distinct Chondroitin Sulfate Form", *Journal of Cellular Physiology* 157:413–425 (1993).

Yeaman et al., "Post–transcriptional Regulation of syndecan–1 Expression by cAMP in Peritoneal Macrophages", *The Journal of Cell Biology*, vol. 122, No. 4, 941–950 (1993).

\* cited by examiner

Nucleotide Sequence Encoding Syndecan-4

```
1    caggagtcgg attctgttcc gttccgattc agcgctccgc accgcctcgc ttcgccatgc
61   cgctgccccg cgccgcgttc ctgctcggcc tcctgctggc cgctgccgcc gccgagtcgg
121  tgagagaaac agagaccatg gatgcccgat ggcttgacaa cgtgggctct ggagacctgc
181  cagatgatga agacattggt gaattcacac ctcacttaac ttctgacgag tttgatatag
241  atgacacatc tggctccgga gactactcag attatgatga tgccatatac ctgaccactg
301  tggatactcc tgcaatatct gacaactata tccctggaga tacagagaga aagatggaag
361  gtgagaagaa aacaccatg ctggacaatg aaatcattcc agacaaagct tcacctgttg
421  aagcaaacct gtccaacaag atctccatgg caagcacagc caacagcagc atctttgaaa
481  gaacagaagt tcttacagct ctcattgcag gaggagcagt tggcctcctg tttgctgtct
541  tcctgatcct cctcttagtc tatcgcatga agaaaaagga cgagggcagc tacgaccttg
601  ggaagaaacc catctacaag aaagccccta caaatgagtt ctacgcttaa agctctgtgc
661  cccttgggac aaatggaccg tatggaaaca ctgtgccctc aatgagacg tgctgaacaa
721  acgctcttt tggattgaat ttcaaagtga cttttgaggg tgggggacca aactttctac
781  gtgacccacc ccgctcagct aacaagggtc caatggaata caaagagtct gggggggggg
841  ttggggggaa gcctcggcgg tgtatctttt tttttt
```

FIG. 1

Amino Acid Sequence of Syndecan-4

SEQUENCE LISTING

<160> NUMBER OF SEQ ID NOS: 2

<210> SEQ ID NO 1
<211> LENGTH: 876
<212> TYPE: DNA
<213> ORGANISM: Homo sapiens
<220> FEATURE:
<221> NAME/KEY: CDS
<222> LOCATION: (57)...(647)

<400> SEQUENCE: 1

```
caggagtcgg attctgttcc gttccgattc agcgctccgc accgcctcgc ttcgcc atg      59
                                                                Met
                                                                  1 ccg ctg ccc cgc gcc gcg ttc ctg ctc ggc ctc ctg gcc gct gcc            107
Pro Leu Pro Arg Ala Ala Phe Leu Leu Gly Leu Leu Ala Ala Ala
              5                  10                  15 gcc gcc gag tcg gtg aga gaa aca gag acc atg gat gcc cga tgg ctt        155
Ala Ala Glu Ser Val Arg Glu Thr Glu Thr Met Asp Ala Arg Trp Leu
         20                  25                  30 gac aac gtg ggc tct gga gac ctg cca gat gat gaa gac att ggt gaa        203
Asp Asn Val Gly Ser Gly Asp Leu Pro Asp Asp Glu Asp Ile Gly Glu
     35                  40                  45 ttc aca cct cac tta act tct gac gag ttt gat ata gat gac aca tct        251
Phe Thr Pro His Leu Thr Ser Asp Glu Phe Asp Ile Asp Asp Thr Ser
 50                  55                  60                  65 ggc tcc gga gac tac tca gat tat gat gat gcc ata tac ctg acc act        299
Gly Ser Gly Asp Tyr Ser Asp Tyr Asp Asp Ala Ile Tyr Leu Thr Thr
```

```
                70              75              80
gtg gat act cct gca ata tct gac aac tat atc cct gga gat aca gag    347
Val Asp Thr Pro Ala Ile Ser Asp Asn Tyr Ile Pro Gly Asp Thr Glu
            85              90              95 aga aag atg gaa ggt gag aag aaa aac acc atg ctg gac aat gaa atc    395
Arg Lys Met Glu Gly Glu Lys Lys Asn Thr Met Leu Asp Asn Glu Ile
        100             105             110 att cca gac aaa gct tca cct gtt gaa gca aac ctg tcc aac aag atc    443
Ile Pro Asp Lys Ala Ser Pro Val Glu Ala Asn Leu Ser Asn Lys Ile
    115             120             125 tcc atg gca agc aca gcc aac agc agc atc ttt gaa aga aca gaa gtt    491
Ser Met Ala Ser Thr Ala Asn Ser Ser Ile Phe Glu Arg Thr Glu Val
130             135             140             145 ctt aca gct ctc att gca gga gga gca gtt ggc ctc ctg ttt gct gtc    539
Leu Thr Ala Leu Ile Ala Gly Gly Ala Val Gly Leu Leu Phe Ala Val
            150             155             160 ttc ctg atc ctc ctc tta gtc tat cgc atg aag aaa aag gac gag ggc    587
Phe Leu Ile Leu Leu Leu Val Tyr Arg Met Lys Lys Lys Asp Glu Gly
        165             170             175 agc tac gac ctt ggg aag aaa ccc atc tac aag aaa gcc cct aca aat    635
Ser Tyr Asp Leu Gly Lys Lys Pro Ile Tyr Lys Lys Ala Pro Thr Asn
    180             185             190 gag ttc tac gct taaagctctg tgccccttgg gacaaatgga ccgtatggaa        687
Glu Phe Tyr Ala
    195 acactgtgcc ctccaatgag acgtgctgaa caaacgctct ttttggattg aatttcaaag  747 tgacttttga gggtggggga ccaaacttc tacgtgaccc accccgctca gctaacaagg   807 gtccaatgga atacaaagag tctgggggggg ggttggggg gaagcctcgg cggtgtatct  867 ttttttttt                                                          876

<210> SEQ ID NO 2
<211> LENGTH: 197
<212> TYPE: PRT
<213> ORGANISM: Homo sapiens

<400> SEQUENCE: 2

Met Pro Leu Pro Arg Ala Ala Phe Leu Leu Gly Leu Leu Ala Ala
 1               5                  10                  15

Ala Ala Ala Glu Ser Val Arg Glu Thr Glu Thr Met Asp Ala Arg Trp
            20                  25                  30

Leu Asp Asn Val Gly Ser Gly Asp Leu Pro Asp Asp Glu Asp Ile Gly
        35                  40                  45

Glu Phe Thr Pro His Leu Thr Ser Asp Glu Phe Asp Ile Asp Asp Thr
    50                  55                  60

Ser Gly Ser Gly Asp Tyr Ser Asp Tyr Asp Ala Ile Tyr Leu Thr
65                  70                  75                  80

Thr Val Asp Thr Pro Ala Ile Ser Asp Asn Tyr Ile Pro Gly Asp Thr
            85                  90                  95

Glu Arg Lys Met Glu Gly Glu Lys Lys Asn Thr Met Leu Asp Asn Glu
        100                 105                 110

Ile Ile Pro Asp Lys Ala Ser Pro Val Glu Ala Asn Leu Ser Asn Lys
    115                 120                 125

Ile Ser Met Ala Ser Thr Ala Asn Ser Ser Ile Phe Glu Arg Thr Glu
130                 135                 140

Val Leu Thr Ala Leu Ile Ala Gly Gly Ala Val Gly Leu Leu Phe Ala
145                 150                 155                 160
```

-continued

```
Val Phe Leu Ile Leu Leu Leu Val Tyr Arg Met Lys Lys Lys Asp Glu
                165                 170                 175

Gly Ser Tyr Asp Leu Gly Lys Lys Pro Ile Tyr Lys Lys Ala Pro Thr
                180                 185                 190

Asn Glu Phe Tyr Ala
            195
```

METHODS OF MODULATING CELL
ATTACHMENT AND MIGRATION

This application claims the benefit of a previously filed Provisional Application No. 60/124,396, filed Mar. 15, 1999, the contents of which is incorporated in its entirety.

BACKGROUND OF THE INVENTION

Adhesion of cells to their surrounding extracellular matrix (ECM) in vivo regulates their morphology, proliferation, migration, survival and differentiation. Adams et al. (1993) *Development* 117:1183–1198; Ashkenas et al. (1996) *Dev. Biol.* 180:433–444; Giancotti (1997) *Curr. Opin. Cell. Biol.* 9:691–700; Howe et al. (1998) *Curr Opin. Cell Biol.* 10:220–231. In vitro, the interactions of cells with ECM molecules such as fibronectin result in cell attachment, spreading and the assembly of focal adhesions and actin stress fibers. Burridge et al. (1996) *Ann. Rev. Cell Dev. Biol.* 12:463–518. Focal adhesions are macromolecular complexes made up of transmembrane adhesion receptors and intracellular proteins with structural and signaling functions. Burridge et al., supra; Clark et al. (1995) *Science* 268:233–239.

Two independent adhesion receptor-mediated signals are required for the assembly of these macromolecular complexes when cells are plated on fibronectin. One signal is mediated through integrins and involves the RGD-containing cell-binding domain of fibronectin. Hynes (1992) *Cell* 69:11–25; Clark et al. (1995) *Science* 268:233–239. The second signal is mediated through cell surface heparan sulfate proteoglycans (HSPGs) and involves heparin-binding domains of fibronectin. Woods et al. (1986) *EMBO J.* 5:665–670.

The formation of complete focal adhesions and stress fibers in the context of integrins has been shown to require integrin clustering, integrin occupancy, tyrosine phosphorylation and cytoskeletal integrity. Hynes (1992) *Cell* 69:11–25; Clark et al. (1995) *Science* 268:233–239; Miyamoto et al. (1995) *J. Cell Biol.* 131:791–805; Miyamoto et al. (1995) *Science* 267:883–885. Integrin signaling pathways involve the small GTP-binding protein Rho. Parsons (1996) *Curr. Opin. Cell Biol.* 8:146–152; small GTP-binding protein Rho. Parsons (1996) *Curr. Opin. Cell. Biol.* 8:146–152; Tapon et al. (1997) *Curr. Topics Cell Biol.* 9:86–92; Clark et al. (1998) *J. Cell Biol.* 142:573–586.

SUMMARY OF THE INVENTION

The present invention is based, at least in part, on the discovery that syndecan-4 acts cooperatively with integrins in generating signals for cell spreading and for the assembly of focal adhesions and actin stress fibers. In addition, it was discovered that these joint signals are regulated in a Rho-dependant manner.

Specifically, it was found that when a cell, which does not express fibronectin, is plated solely on the cell binding domain of fibronectin or antibodies directed against the β integrin chain, the cell attaches but fails to spread or assemble focal adhesions or actin stress fibers. When antibodies directed against the ectodomain of syndecan-4 are then added, the cells spread fully and assemble focal adhesions and actin stress fibers which are indistinguishable from cells plated on fibronectin. Moreover, it was found that the activation of the GTP-binding protein Rho, which is a key regulator in adhesion-mediated signaling events through integrins, is also dependent on syndecan-4 signaling events.

Accordingly, in one aspect, the invention features, a method of modulating the spatial or positional relationship of a cell to a substrate, or modulating the intracellular response of a cell to a substrate, in vitro or in vivo. The spatial or positional relationship of a cell to a substrate refers to the spatial or positional relationship of one or more points on the cell to substrate, and includes, e.g., cell attachment, cell spreading, or cell migration. Cell spreading includes the movement of an entire cell across a substrate as well as the movement of one part of the cell but not another part of the cell with regard to the substrate. The intracellular response of a cell to a substrate refers the response, e.g., the movement or formation or disolution of, a cellular component, e.g., a cell membrane protein, or an actin stress fiber, to a substrate and includes the formation or dissolution of a focal adhesion.

The method includes administering an agent which modulates the interaction, e.g., the binding, of the syndecan-4 ectodomain with a counterligand, thereby modulating the spatial or positional relationship of a cell to a substrate, or modulating the intracellular response of a cell to a substrate. The preferred counterligand is an ECM component, e.g., the heparin-binding domain of a component of the extracellular matrix (ECM) such as fibronectin, vitronectin, a laminin or a collagen.

In a preferred embodiment, the agent inhibits syndecan-4 ectodomain binding to a counterligand, e.g., the heparin-binding domain of an ECM molecule. The spatial or positional relationship of a cell to a substrate, or the intracellular response of a cell to a substrate, can be inhibited or reduced by interfering with the interaction of syndecan-4 a counterligand, e.g., a heparin-binding domain of an ECM molecule. Agents which interfere with the binding of syndecan-4 to a counterligand include agents which bind to an ECM molecule, such as fibronectin, vitronectin, a laminin or a collagen, and thereby inhibit the binding of the ectodomain of syndecan-4, with a heparin-binding domain of the ECM molecule. The invention is not limited by the particular mechanism of inhibition. The agent can e.g., act: by binding and occupying the site normally bound by the ectodomain of syndecan-4, by binding to and changing the shape of the ECM molecule (such that counterligand binding is inhibited); or by binding an ECM molecule and sterically hindering binding of the ectodomain of syndecan-4 to a heparin-binding domain of the molecule. Examples of such agents include: a syndecan-4 protein, e.g., a soluble syndecan4 protein, or a heparin binding domain (HBD)-binding portion thereof, e.g., from amino acid residues 90 to 120 of SEQ ID NO:2; a fusion of a syndecan-4 protein, e.g., a fusion of syndecan-4, or a HBD-binding portion thereof, to another polypeptide, e.g., a polypeptide which promotes solubility or which targets or binds to a substrate; a polypeptide other than syndecan-4 which binds to an ECM molecule, e.g., to a heparin binding domain of an ECM molecule, e.g., a polypeptide selected for binding in, e.g., a phage display or 2 hybrid assay; antibodies to an ECM molecule, e.g., antibodies which bind the site normally bound by the ectodomain of syndecan-4, antibodies which bind to and change the shape of the ECM molecule, or antibodies which bind and sterically hinder binding of the ectodomain of syndecan-4 to a heparin-binding domain of an ECM molecule. ECM molecules include, for example, fibronectin, vitronectin, laminins and collagens.

In a preferred embodiment, the method includes administering a nucleic acid which encodes one of the above-described agents.

The inhibitory agent can act by binding syndecan-4. While not wishing to be bound by theory these agents may bind to syndecan-4 but fail to provide, or otherwise inhibit the transduction of a signal which normally arises when syndecan-4 binds to a heparin-binding domain of an ECM molecule. These agents can e.g., bind and occupy the site on the ectodomain of syndecan-4 normally bound by a heparin-binding domain of an ECM molecule; bind to and change the shape of syndecan-4; or bind and sterically hinder binding of a heparin-binding domain of an ECM molecule to the ectodomain of syndecan-4. Examples of such agents include an analog of fibronectin or of a syndecan-4 binding portion of fibronectin; an analog of vitronectin or of a syndecan-4 binding portion of vitronectin; an analog of a laminin or of a syndecan-4 binding portion of a laminin; an analog of a collagen or of a syndecan-4 binding portion of a collagen; an analog of a soluble heparin binding domain; a fusion of all, or a syndecan-4 protein binding portion, of an analog of an EMC molecule to another polypeptide, e.g., a polypeptide which promotes solubility or which targets or binds to a substrate; a polypeptide other than a heparin binding domain which binds to the ectodomain of syndecan-4, e.g., a polypeptide selected for binding in, e.g., a phage display or 2 hybrid assay; or an antibody which binds the ectodomain of syndecan-4, e.g., antibodies which bind the ectodomain of syndecan-4 and inhibit the transduction of a signal which normally arises when syndecan-4 binds to a heparin-binding domain of an ECM molecule. These agents can be found by selecting for species which bind to the ectodomain of syndecan-4 but which result in a less than normal level of cell spreading or the formation of focal adhesions. A two part screen can be used wherein binding is selected for in an in vitro or cell free assay and activity is selected for in a cell based assay. In a preferred embodiment, the method includes administering a nucleic acid which encodes one of the above-described agents.

In another preferred embodiment, the agent promotes cell spreading, cell attachment, cell migration, or the formation of a focal adhesion. While not wishing to be bound by theory, these agents are believed to act by mimicking (or agonizing) the binding of a heparin binding domain of an ECM molecule such as fibronectin to the ectodomain of syndecan-4. These agents can bind the site on the ectodomain of syndecan-4 normally bound by a heparin-binding domain of an ECM molecule. Examples of such agents include: fibronectin, or a syndecan-4 binding portion of fibronectin; vitronectin, or a syndecan-4 binding portion of vitronectin; a laminin, or a syndecan-4 binding portion of a laminin; a collagen, or a syndecan-4 binding portion of a collagen; a soluble a heparin binding domain; a fusion of all or a syndecan-4 protein binding portion of an ECM molecule to another polypeptide, e.g., a polypeptide which promotes solubility or which targets or binds to a substrate; a polypeptide other than a heparin binding domain which binds to the ectodomain of syndecan-4, e.g., a polypeptide selected for binding in, e.g., a phage display or 2 hybrid assay; or an antibody which binds the ectodomain of syndecan-4. These agents can be found by selecting for species which bind to the ectodomain of syndecan-4 and which result in cell spreading or the formation of focal adhesions. A two part screen can be used wherein binding is selected for in an in vitro or cell free assay and activity is selected for in a cell based assay. In a preferred embodiment, the method includes administering a nucleic acid which encodes one of the above-described agents.

In a preferred embodiment, the method of promoting cell attachment, cell spreading, migration, or the formation of a focal adhesion, further comprises administering an agent which promotes integrin binding, e.g., an anti-integrin antibody. Preferably, the antibody is an anti-$\beta 1$ integrin chain antibody. Other agents which promote integrin binding include: a fibronectin protein, e.g., the cell binding domain (CBD) portion of fibronectin, e.g., the RGD sequence of the CBD; a vitronectin protein, e.g., the CBD portion of vitronectin; a laminin protein, e.g., the CBD portion of a laminin; a collagen protein, e.g., the CBD portion of a collagen; a polypeptide other than an ECM molecule which binds to a $\beta 1$ chain of integrin, e.g., a polypeptide which binds to a CBD-binding portion of integrin, e.g., a polypeptide selected for binding in, e.g., a phage display or 2 hybrid assay; a small molecule, e.g., a small molecule capable of binding a $\beta 1$ chain of integrin, e.g., a small molecule capable of binding a CBD-binding portion of integrin. In a preferred embodiment, the method includes administering a nucleic acid which encodes one of the above-described agents.

In a preferred embodiment, the method modulates, e.g., inhibits or promotes, cell attachment and/or spreading by: modulating focal adhesion assembly; modulating actin stress fiber formation; modulating an adhesion-mediated signaling pathway, e.g., modulating a Rho-dependent adhesion pathway; modulating the interaction, e.g., binding, with a component of the extracellular matrix, e.g., fibronectin, vitronectin, a laminin, or a collagen.

In a preferred embodiment, the method includes treating a subject having a disorder characterized by unwanted or abnormal cellular interactions (e.g., unwanted or abnormal cell-cell and/or cell-matrix interactions, unwanted or abnormal cell migration/movement, e.g., cancer).

In another aspect, the invention features a method of modulating the spatial or positional relationship of a cell to a substrate, or modulating the intracellular response of a cell to a substrate.

In a preferred embodiment, the invention features a method of inhibiting syndecan-4 ectodomain binding to a counterligand, e.g., the heparin binding domain of an ECM molecule, and an agent which inhibits integrin binding. Agents which interfere with the binding of syndecan-4 to a counterligand include agents which bind to an ECM molecule (e.g., fibronectin, vitronectin, a laminin, or a collagen) and thereby inhibit the binding of the ectodomain of syndecan-4, with a heparin-binding domain of the ECM molecule. The invention is not limited by the particular mechanism of inhibition. The agent can, e.g., act: by binding and occupying the site normally bound by the ectodomain of syndecan-4, by binding to and changing the shape of the ECM molecule (such that counterligand binding is inhibited); or by binding an ECM molecule and sterically hindering binding of the ectodomain of syndecan-4 to a heparin-binding domain of the ECM molecule. Examples of such agents include: a syndecan-4 protein, e.g., a soluble syndecan-4 protein, or a HBD-binding portion thereof e.g., from about amino acids 90 to 120 of SEQ ID NO:2; a fusion of a syndecan-4 protein, e.g., a fusion of syndecan-4, or a HBD-binding portion thereof, to another polypeptide, e.g., a polypeptide which promotes solubility or which targets or binds to a substrate; a polypeptide other than syndecan-4 which binds to an ECM molecule e.g., to a heparin binding domain of an ECM molecule, e.g., a polypeptide selected for binding in, e.g., a phage display or 2 hybrid assay; antibodies to an ECM molecule, e.g., antibodies which bind the site normally bound by the ectodomain of syndecan-4, antibodies which bind to and change the shape of the ECM molecule, or antibodies which bind and sterically hinder binding of the ectodomain of syndecan-4 to a heparin-binding domain of an ECM molecule.

In a preferred embodiment, the agent which inhibits or reduces integrin binding is: an integrin protein, e.g., a soluble integrin protein, or a CBD-binding portion thereof; a fusion of an integrin protein, e.g., a fusion of a integrin, or a CBD-binding portion thereof, to another polypeptide, e.g., a polypeptide which promotes solubility; a polypeptide other than integrin which binds to a cell binding domain of fibronectin, e.g., a polypeptide selected for binding in, e.g., a phage display or 2 hybrid assay; antibodies to an ECM molecule, e.g., antibodies which bind to the site normally bound by integrin, antibodies which bind to and change the shape of the ECM molecule, or antibodies which bind and sterically hinder binding of the cell binding domain-binding portion of integrin. In a preferred embodiment, the method includes administering a nucleic acid which encodes one of the above-described agents.

The inhibitory agent can act by binding syndecan-4. While not wishing to be bound by theory these agents may bind to syndecan-4 but fail to provide, or otherwise inhibit the transduction of a signal which normally arises when syndecan-4 binds to a heparin-binding domain of an ECM molecule. These agents can e.g., bind and occupy the site on the ectodomain of syndecan-4 normally bound by a heparin-binding domain of an ECM molecule; bind to and change the shape of syndecan-4; or bind and sterically hinder binding of a heparin-binding domain of an ECM molecule to the ectodomain of syndecan-4. Examples of such agents include an analog of fibronectin or of a syndecan-4 binding portion of fibronectin; an analog of vitronectin or of a syndecan-4 binding portion of vitronectin; an analog of a laminin or of a syndecan-4 binding portion of a laminin; an analog of a collagen or of a syndecan-4 binding portion of a collagen; an analog of a soluble heparin binding domain; a fusion of all, or a syndecan-4 protein binding portion, of an analog of an ECM molecule to another polypeptide, e.g., a polypeptide which promotes solubility or which targets or binds to a substrate; a polypeptide other than a heparin binding domain which binds to the ectodomain of syndecan-4, e.g., a polypeptide selected for binding in, e.g., a phage display or 2 hybrid assay; or an antibody which binds the ectodomain of syndecan-4, e.g., antibodies which bind the ectodomain of syndecan-4 and inhibit the transduction of a signal which normally arises when syndecan-4 binds to a heparin-binding domain of an ECM molecule. These agents can be found by selecting for species which bind to the ectodomain of syndecan-4 but which result in a less than normal level of cell spreading or the formation of focal adhesions. A two part screen can be used wherein binding is selected for in an in vitro or cell free assay and activity is selected for in a cell based assay. In a preferred embodiment, the method includes administering a nucleic acid which encodes one of the above-described agents.

In another preferred embodiment, the invention features a method of promoting cell attachment, cell spreading, migration, or the formation of a focal adhesion. The method includes administering an agent which promotes syndecan-4 ectodomain binding and an agent which promotes integrin binding. Agents which promote syndecan-4 ectodomain binding can bind the site on the ectodomain of syndecan-4 normally bound by a heparin-binding domain of an ECM molecule. Examples of such agents include: fibronectin, or a syndecan-4 binding portion of fibronectin; vitronectin, or a syndecan-4 binding portion of vitronectin; a laminin, or a syndecan-4 binding portion of a laminin; a collagen, or a syndecan-4 binding portion of a collagen; a soluble a heparin binding domain; a fusion of all or a syndecan-4 binding portion of an ECM molecule to another polypeptide, e.g., a polypeptide which promotes solubility; a polypeptide other than a heparin binding domain which binds to the ectodomain of syndecan-4, e.g., a polypeptide selected for binding in, e.g., a phage display or 2 hybrid assay; or an antibody which binds the ectodomain of syndecan-4. These agents can be found by selecting for species which bind to the ectodomain of syndecan-4 and which result cell spreading or the formation of focal adhesions. In a preferred embodiment, the method includes administering a nucleic acid which encodes one of the above-described agents.

In a preferred embodiment, the agent which promotes integrin binding is: an anti-integrin antibody, e.g., an anti-$\beta 1$ integrin chain antibody; a fibronectin protein, e.g., the CBD portion of fibronectin, e.g., the RGD sequence of the CBD; a vitronectin, or an integrin binding portion of vitronectin; a laminin, or an integrin binding portion of a laminin; a collagen, or an integrin binding portion of a collagen; a polypeptide other than an ECM molecule which binds to a $\beta 1$ chain of integrin, e.g., a CBD-binding portion of integrin, e.g., a polypeptide selected for binding in, e.g., a phage display or 2 hybrid assay; a small molecule, e.g., a small molecule capable of binding a $\beta 1$ chain of integrin, e.g., a CBD-binding portion of integrin. In a preferred embodiment, the method includes administering a nucleic acid which encodes one of the above-described agents.

In a preferred embodiment, the method modulates, e.g., inhibits or promotes, cell attachment and/or spreading by: modulating focal adhesion assembly; modulating actin stress fiber formation; modulating an adhesion-mediated signaling pathway e.g., a Rho dependent adhesion pathway; modulating the interaction, e.g., binding, with a component of the extracellular matrix, e.g., fibronectin, vitronectin, a laminin, a collagen.

In a preferred embodiment, the method includes treating a subject having a disorder characterized by unwanted or abnormal cellular interactions (e.g., unwanted or abnormal cell-cell and/or cell-matrix interactions, unwanted or abnormal cell migration/movement, e.g., cancer).

Another aspect of the invention features a method of identifying a compound or agent which modulates the spatial or positional relationship of a cell to a substrate, or modulating the intracellular response of a cell to a substrate.

In a preferred embodiment, the compound inhibits or reduces cell attachment, cell spreading, migration or the formation of a focal adhesion. A compound can include, for example, a fragment or analog of syndecan-4, a polypeptide other than syndecan-4, e.g., a randomly generated polypeptide which interacts with an ECM molecule, e.g., interacts with the heparin binding domain of an ECM molecule; or a small molecule, e.g., a small molecule which interacts with an ECM molecule, e.g., interacts with the heparin binding domain of an ECM molecule. In a preferred embodiment, the method can include the steps of forming a reaction mixture which includes a polypeptide comprising the heparin binding domain of an ECM molecule and a compound or agent under conditions which allow for the binding of the compound to the heparin binding domain to form a complex and detecting the formation of a complex of the heparin binding domain and the compound, in which the ability of the compound to bind the heparin binding domain is indicated by the presence of the compound in complex.

Methods for identifying a compound or an agent can be performed, for example, using a cell free assay. For example, the heparin binding domain of an ECM molecule such as fibronectin can be immobilized to a suitable substrate, e.g., glutathoine sepharose beads or glutathoine derivatized microtitre plates, using a fusion protein which allows for the heparin binding domain to bind to the substrate, e.g., a glutathoine-S-transferase/heparin binding domain fusion protein.

In a preferred embodiment, the method further comprises adding syndecan-4, or a polypeptide comprising the heparin binding domain-binding region of syndecan-4, to the reaction mixture.

In a preferred embodiment, a compound can be identified using a cell-based assay. These methods include identifying a compound based on its ability to modulate, e.g., inhibit, an adhesion-mediated activity of the cell. Example of such adhesion mediated activities include: inhibiting focal adhesion assembly, inhibiting actin stress fiber formation; inhibiting an adhesion-mediated signaling pathway, e.g., a Rho dependent signaling pathway; inhibiting the interaction, e.g., binding, with a component of the extracellular matrix, e.g., fibronectin, vitronectin, a laminin, or a collagen.

In another preferred embodiment, the compound promotes or increases cell attachment, cell spreading, migration or formation of a focal adhesion. A compound can include, for example, an analog of fibronectin, e.g., an analog of the heparin binding domain; an analog of vitronectin, or a syndecan-4 binding portion of vitronectin; an analog of a laminin, or a syndecan-4 binding portion of a laminin; an analog of a collagen, or a syndecan-4 binding portion of a collagen; a polypeptide other than an EMC molecule, e.g., a randomly generated polypeptide which interacts with the syndecan-4, e.g., the HBD-binding portion of syndecan-4; or a small molecule, e.g., a small molecule which interacts with syndecan-4, e.g., the ectodomain of syndecan-4, e.g., the HBD-binding portion of syndecan-4. In a preferred embodiment, the method can include the steps of forming a reaction mixture which includes a polypeptide comprising the HBD-binding portion of syndecan-4, with a compound or agent under conditions which allow for the binding of the compound to the HBD-binding portion to form a complex and detecting the formation of a complex of the HBD-binding portion and the compound, in which the ability of the compound to bind the HBD-binding portion of syndecan-4 is indicated by the presence of the compound in complex.

Methods for identifying a compound or an agent can be performed, for example, using a cell free assay. For example, the HBD-binding portion of syndecan-4 can be immobilized to a suitable substrate, e.g., glutathoine sepharose beads or glutathoine derivatized microtitre plates, using a fusion protein which allows for the HBD-binding portion to bind to the substrate, e.g., a glutathoine-S-transferase/HBD-binding portion of syndecan-4 fusion protein.

In a preferred embodiment, a compound can be identified using a cell based assay. These methods include identifying a compound based on its ability to modulate, e.g., promote, an adhesion-mediated activity of the cell. Example of such adhesion mediated activities include: promoting focal adhesion assembly, promoting actin stress fiber formation; promoting an adhesion-mediated signaling pathway, e.g., a Rho dependent signaling pathway; promoting the interaction, e.g., binding, with a component of the extracellular matrix, e.g., fibronectin, vitronectin, a laminin, a collagen.

In another aspect, the invention features a method of identifying a compound which modulates, e.g., inhibits or promotes, the interaction of syndecan-4 ectodomain with an agent which binds to syndecan4, e.g., a heparin binding domain of an ECM molecule. ECM molecules include fibronectin, vitronectin, laminins, and collagen. In these methods, a polypeptide comprising the heparin binding domain of an ECM molecule is contacted, in the presence a compound or agent, with syndecan-4, or a portion thereof, under conditions which allow binding of the heparin binding domain and syndecan-4. An alteration, e.g., an increase or decrease, in complex formation between the heparin binding domain and syndecan-4, as compared to the amount formed in the absence of the compound or agent is indicative of ability of the compound to modulate the interaction of the heparin binding domain and syndecan-4.

Another aspect of the invention features a method of identifying a compound which modulates, inhibits or reduces, cell attachment and/or spreading. The method includes contacting a polypeptide comprising the heparin binding domain of an ECM molecule with a compound or agent in the presence of a cell which expresses syndecan-4, or a portion thereof, and detecting the presence or absence of an adhesion-mediated activity by the cell. These methods can include detecting the following adhesion mediated activities: modulation of focal adhesion assembly; modulation actin stress fiber formation; modulation an adhesion-mediated signaling pathway, e.g., a Rho-dependent signaling pathway; modulation the interaction, e.g., binding with a component of the extracellular matrix, e.g., fibronectin, vitronectin, a laminin, a collagen. Such compounds can include, for example, a fragment or analog of syndecan-4, a polypeptide other than syndecan-4, e.g., a randomly generated polypeptide which interacts with an ECM molecule, e.g., the heparin binding domain of an ECM molecule; or a small molecule, e.g., a small molecule which interacts with an ECM molecule, e.g., a small molecule which interacts with the heparin binding domain of an ECM molecule. In addition, a compound can bind to syndecan-4, e.g., the ectodomain of syndecan-4, without generating adhesion-mediated signals. Such compounds can include, for example, an analog of a heparin binding domain which binds to syndecan-4 but does not generate adhesion-mediated signaling; a polypeptide other than a heparin binding domain, e.g., a randomly generated polypeptide which does not bind the HBD-binding portion of syndecan-4, but blocks binding of other agents to the HBD-binding portion of syndecan-4, or a randomly generated polypeptide which binds to the HBD-binding portion of syndecan-4 but does not generate adhesion-mediated signaling; or a small molecule, e.g., a small molecule which does not bind the HBD-binding portion of syndecan-4, but blocks binding of other agents to the HBD-binding portion of syndecan-4, or a small molecule which binds to the HBD-binding portion of syndecan-4 but does not generate adhesion-mediated signaling.

In another aspect, the invention features, a method of treating a subject having a disorder characterized by unwanted or abnormal cell adhesion or cell spreading (e.g., cancer). The method includes administering to the subject an agent which modulates, e.g., inhibits, the binding of syndecan-4 with a couterligand, thereby modulating, e.g., inhibiting, cell adhesion or cell spreading.

In a preferred embodiment, the agent inhibits syndecan4 ectodomain binding to a counterligand, e.g., an ECM molecule, e.g., the heparin-binding domain of an ECM molecule. The spatial or positional relationship of a cell to a substrate, or the intracellular response of a cell to a substrate, can be inhibited or reduced by interfering with the interaction of syndecan4 a counterligand, e.g., a heparin-binding domain of an ECM molecule. Examples of ECM molecules include fibronectin, vitronectin, laminins and collagen. Agents which interfere with the binding of syndecan-4 to a counterligand include agents which bind to an ECM molecule, e.g., a heparin binding domain of an ECM molecule, and thereby inhibit the binding of the ectodomain of syndecan-4, with a heparin-binding domain of the ECM molecule. The invention is not limited by the particular mechanism of inhibition. The agent can e.g., act: by binding and occupying the site normally bound by the ectodomain of syndecan-4, by binding to and changing the shape of the ECM molecule (such that counterligand binding is inhibited); or by binding an ECM molecule and sterically hindering binding of the ectodomain of syndecan4 to a heparin-binding domain of an ECM molecule. Examples of such agents include: a syndecan-4 protein, e.g., a soluble syndecan-4 protein, or a HBD-binding portion thereof e.g., from about amino acids 90 to 120 of SEQ ID NO:2; a fusion of a syndecan-4 protein, e.g., a fusion of syndecan-4, or a HBD-binding portion thereof, to another polypeptide, e.g., polypeptide which promotes solubility or which targets or binds to a substrate; a polypeptide other than syndecan-4 which binds to an ECM molecule, e.g., to a heparin binding domain of an ECM molecule, e.g., a polypeptide selected for binding in, e.g., a phage display or 2 hybrid assay; antibodies to an ECM molecule, e.g., antibodies which bind the site normally bound by the ectodomain of syndecan-4, antibodies which bind to and change the shape of the ECM molecule, or antibodies which bind and sterically hinder binding of the ectodomain of syndecan-4 to a heparin-binding domain of an ECM molecule.

In a preferred embodiment, the method includes administering a nucleic acid which encodes one of the above-described agents.

The inhibitory agent can act by binding syndecan-4. While not wishing to be bound by theory these agents may bind to syndecan-4 but fail to provide, or otherwise inhibit the transduction of a signal which normally arises when syndecan-4 binds to a heparin-binding domain of an ECM molecule, e.g., fibronectin, vitronectin, a laminin, or a collagen. These agents can e.g., bind and occupy the site on the ectodomain of syndecan-4 normally bound by a heparin-binding domain of an ECM molecule; bind to and change the shape of syndecan-4; or bind and sterically hinder binding of a heparin-binding domain of an ECM molecule to the ectodomain of syndecan-4. Examples of such agents include an analog of fibronectin, or a syndecan-4 binding portion of fibronectin; an analog of vitronectin, or a syndecan-4 binding portion of vitronectin; an analog of a laminin, or a syndecan4 binding portion of a laminin; an analog of a collagen, or a syndecan-4 binding portion of a collagen; an analog of a soluble heparin binding domain of an ECM molecule; a fusion of all, or a syndecan-4 protein binding portion, of an ECM molecule to another polypeptide, e.g., a polypeptide which promotes solubility or which targets or binds to a substrate; a polypeptide other than a heparin binding domain which binds to the ectodomain of syndecan-4, e.g., a polypeptide selected for binding in, e.g., a phage display or 2 hybrid assay; or an antibody which binds the ectodomain of syndecan-4. These agents can be found by selecting for species which bind to the ectodomain of syndecan-4 but which result in a less than normal level of cell spreading or the formation of focal adhesions. A two part screen can be used wherein binding is selected for in an in vitro or cell free assay and activity is selected for in a cell based assay. In a preferred embodiment, the method includes administering a nucleic acid which encodes one of the above-described agents.

In a preferred embodiment, the method further comprises administering an agent which inhibits integrin binding. Agents which inhibit or reduce integrin binding include: an integrin protein, e.g., a soluble integrin protein, or a CBD-binding portion thereof; a fusion of an integrin protein, e.g., a fusion of a integrin, or a CBD-binding portion thereof, to another polypeptide, e.g., a polypeptide which promotes solubility; a polypeptide other than integrin which binds to a cell binding domain of an ECM molecule, e.g., a polypeptide selected for binding in, e.g., a phage display or 2 hybrid assay; antibodies to an ECM molecule, e.g., antibodies which bind to the site normally bound by integrin, antibodies which bind to and change the shape of an ECM molecule, or antibodies which bind and sterically hinder binding of the cell binding domain-binding portion of integrin. In a preferred embodiment, the method includes administering a nucleic acid which encodes one of the above-described agents.

In a preferred embodiment, the method modulates, e.g., inhibits, cell attachment and/or spreading by: modulating focal adhesion assembly; modulating actin stress fiber formation; modulating an adhesion-mediated signaling pathway, e.g., modulating a Rho-dependent adhesion pathway; modulating the interaction, e.g., binding, with a component of the extracellular matrix, e.g., fibronectin, vitronectin, a laminin, a collagen.

Another aspect of the invention features a method of treating a subject having a disorder characterized by abnormal cell adhesion or cell spreading. The method includes administering to the subject an agent which modulates, e.g., promotes, the binding of syndecan-4 with a couterligand, thereby modulating, e.g., promoting, cell adhesion or cell spreading.

In a preferred embodiment, the agent promotes cell spreading, cell attachment, cell migration, or the formation of a focal adhesion. While not wishing to be bound by theory, these agents are believed to act by mimicking (or agonizing) the binding of a heparin binding domain of an ECM molecule to the ectodomain of syndecan-4. These agents can bind the site on the ectodomain of syndecan-4 normally bound by a heparin-binding domain of an ECM molecule. Examples of such agents include: fibronectin, or a syndecan-4 binding portion of fibronectin; vitronectin, or a syndecan-4 binding portion of vitronectin; a laminin, or a syndecan-4 binding portion of a laminin; a collagen, or a syndecan-4 binding portion of a collagen; a soluble a heparin binding domain of an ECM molecule; a fusion of all or a syndecan-4 protein binding portion of an ECM molecule to another polypeptide, e.g., a polypeptide which promotes solubility or which targets or binds to a substrate; a polypeptide other than a heparin binding domain which binds to the ectodomain of syndecan-4, e.g., a polypeptide selected for binding in, e.g., a phage display or 2 hybrid assay; or an antibody which binds the ectodomain of syndecan-4. These agents can be found by selecting for species which bind to the ectodomain of syndecan-4 and which result in cell spreading or the formation of focal adhesions. A two part screen can be used wherein binding is selected for in an in vitro or cell free assay and activity is selected for in a cell based assay. In a preferred embodiment, the method includes administering a nucleic acid which encodes one of the above-described agents.

In a preferred embodiment, the method of promoting cell attachment, cell spreading, migration, or the formation of a focal adhesion, further comprises administering an agent which promotes integrin binding, e.g., an anti-integrin antibody. Preferably, the antibody is an anti-$\beta$1 chain antibody. Other agents which promote integrin binding include: a fibronectin protein, e.g., the CBD portion of fibronectin, e.g., the RGD sequence of the CBD; a vitronectin, e.g., a CBD portion of vitronectin; a laminin, or a CBD portion of a laminin; a collagen, or a CBD of a collagen; a polypeptide other than an ECM molecule which binds to a $\beta$1 chain of integrin, e.g., a polypeptide which binds to a CBD-binding portion of integrin, e.g., a polypeptide selected for binding in, e.g., a phage display or 2 hybrid assay; a small molecule, e.g., a small molecule capable of binding a β1 chain of integrin, e.g., a small molecule capable of binding a CBD-binding portion of integrin. In a preferred embodiment, the method includes administering a nucleic acid which encodes one of the above-described agents.

In a preferred embodiment, the method modulates, e.g., promotes, cell attachment and/or spreading by: modulating focal adhesion assembly; modulating actin stress fiber formation; modulating an adhesion-mediated signaling pathway, e.g., modulating a Rho-dependent adhesion pathway; modulating the interaction, e.g., binding, with a component of the extracellular matrix, e.g., fibronectin, vitronectin, a laminin, a collagen.

The term "treatment", as used herein, refers to any therapeutic treatment, e.g., the administration of a therapeutic agent or substance, e.g., a drug.

As used herein, the term "subject" refers to human and non-human animals. In preferred embodiments, the subject is a human, e.g., a person having or diagnosed as at risk for a disorder characterized by aberrant or unwanted cell attachment and/or spreading. The term "non-human animals" of the invention includes all vertebrates, e.g., mammals and non-mammals, such as non-human primates, ruminants, birds, amphibians, and reptiles.

The terms "peptides", "proteins" and "polypeptides" are used interchangeably herein.

The term "small molecules" as used herein refers, to a molecule which has a molecular weight of less than 2,000, preferably less than 1,000. Examples of small molecules include peptides, peptidomimitics, and non-peptidic compounds such as organic molecules. Such molecules can bind to an ECM molecule, e.g., the HBD of an ECM molecule, to inhibit or reduce syndecan-4 binding or can bind to syndecan-4 to either inhibit or reduce the binding of syndecan-4 to an ECM molecule, e.g., HBD, or can bind the syndecan-4 to promote cell adhesion.

The term "ectodomain" refers to the extracellular portion of sydecan-4.

An "adhesion mediated activity", as used herein, refers to activities of a cell which modulate the spatial or positional relationship of a cell to a substrate or modulates the intracellular response of a cell to a substrate. The "spatial or positional relationship of a cell to a substrate" refers to the spatial or positional relationship of one or more points on the cell to substrate, and includes e.g., cell attachment, cell spreading, or cell migration. Cell spreading includes the movement of an entire cell across a substrate as well as the movement of one part of the cell but not another part of the cell with regard to the substrate. The "intracellular response of a cell to a substrate" refers the response, e.g., the movement or formation or disolution of, a cellular component, e.g., a cell membrane protein, or an actin stress fiber, to a substrate and includes the formation or dissolution of a focal adhesion. Responses of the cell can also include activation of various intracellular proteins.

The term "substrate" as used herein refers to a substrate on which cells can adhere, spread, migrate or form a focal adhesion either in vivo, or in vitro. In vivo examples include a basement membrane, a layer of cells, or the surface of an organ or tissue. Generally this is mediated by a counterligand on or in the substrate. A counterligand can be a component of the ECM, e.g., components of the extracellular matrix such as fibronectin, vitronectin, laminins, and collagens, as well as components of other cells which provide for attachment.

The practice of the present invention will employ, unless otherwise indicated, conventional techniques of cell biology, cell culture, molecular biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

Other features and advantages of the invention will be apparent from the following detailed description, and from the claims.

BRIEF DESCRIPTION OF THE DRAWINGS

FIG. 1 depicts the nucleotide sequence encoding syndecan-4 (SEQ.ID NO:1).

FIG. 2 depicts the amino acid sequence of syndecan-4 (SEQ ID NO:2).

DETAILED DESCRIPTION OF THE INVENTION

The present invention is based, at least in part, on the discovery that syndecan-4 acts cooperatively with integrins in generating signals for cell spreading and for the assembly of focal adhesions and actin stress fibers.

Actin filaments can bind to the plasma membrane of a cell in a manner that allows for the fibers to pull on the extracellular matrix or on another cell. These contacts and actin fibers allow a cell attached to the extracellualr matrix or to other cells to migrate. In addition, attachment of a cell to the extracellular matrix or other cells to differentiate and/or proliferate. Once cell adhesion occurs, cell-adhesion mediated events result in the activation of a number of signaling pathways that lead to the formation of focal adhesions and actin stress fibers in cells. The attachment of actin fibers to the plasma membrane is usually mediated by transmembrane glycoproteins in the plasma membrane of the cell which interact with extracellular matrix components such as fibronectin, vitronectin, laminins and/or collagen. These adhesion-mediated pathways control the activation of protein tyrosine kinases and members of the small GTP-binding protein Rho.

Two independent adhesion receptor mediated signals are required for the assembly of focal contacts and actin stress fibers with extracellular matrix components such as fibronectin, vitronectin, laminins, and/or collagens. One signal is mediated through integrins and involves the RGD sequence of the cell-binding domain (CBD) of fibronectin. Clark et al (1995) *Science* 268:233–239; Hynes (1992) *Cell* 69:11–25; and Schwartz et al. (1995) *Annu. Rev. Cell. Dev. Biol.* 11:549–599. The second signal is mediated by cell surface heparan sulfate proteoglycans and involves the heparin binding domain (HBD) of an ECM molecule. Specifically, the second signal is mediated by syndecan-4.

Using cells lacking fibronectin expression, it was discovered not only that syndecan-4 acts cooperatively with integrins in the assembly of focal adhesions and actin stress fibers with fibronectin, but also that even without the presence of the HBD of fibronectin, syndecan-4 can bind to anti-syndecan-4 antibodies to promote cell spreading and the assembly of focal adhesions and actin fibers. In the presence of the CBD of fibronectin and anti-syndecan-4 antibodies, cells are able to spread extensively and assemble focal adhesions and actin fibers that are indistinguishable from cells plated on intact fibronectin. However, syndecan-4 antibodies alone, without the presence of the CBD or anti-$\beta 1$ integrin antibodies have no effect. Thus, the occupancy of integrins alone or syndecan-4 alone is not sufficient for full spreading and assembly of focal adhesions or actin stress fibers. Rather, occupancy of both integrin and syndecan-4 is required for complete cellular adhesion response.

EXAMPLES

Generation of Fibronectin-/-Embryonic Stem Cells

The fibronectin ($Fn^{1mlHyn}$) null mutation was obtained on a 129Sv/Jae background by breeding a chimeric founder with 129Sv/Jae females as described in George et al. (1993) *Development* 119:1079–1091. Heterozygous $Fn^{1mlHyn}$ animals were bred to obtain time-mated females (day 0.5=noon on the day of vaginal plug identification). To delay implantation, 2.5 days post coitum (dpc), females were ovariectomized and injected subcutaneously with 0.15 ml of a 10 mg/ml solution of Depo-Provera (M1629, Sigma, St. Louis, Mo.) in physiological saline. Six and a half dpc, blastocysts were flushed from uterine horns using ES cell medium (as described in George et al., supra) supplemented with 1000 U/ml lymphocyte inhibitory factor and cultured on a feeder layer of embryonic fibroblasts in gelatin-coated 4-well plates (Nunc). Ten and a half dpc, the expanded inner cell masses from cultured blastocysts were picked using a drawn-out Pasteur pipette and trypsinized for 10 minutes at 37° C. in 3 $\mu$l of trypsin (0.25%)/EDTA. Single-cell suspensions were re-plated on feeder layers in 4-well plates. Fifteen and a half dpc, clones were trypsinized and transferred to a 12-well plate (passage 0). Clones were expanded to passage 3 and aliquots were stored at -135° C. DNA from passage 3 clones was analyzed by PCR as previously described in George et al., supra. From approximately 20 original blastocysts, 2 independent null embryonic stem (ES) cell clones were generated.

Numerous attempts to obtain fibronectin-/-ES cells from previously isolated heterozygous cells using selection in high concentrations of G418 failed to yield any homozygous lines. See George et al. (1993) *Development* 119:1079–1091. Accordingly, in these experiments, fibronectin-/-ES cells were generated by deriving new ES cell lines from blastocysts arising from intercrosses of FN-null heterozygotes on a 129Sv/Jae background by established methods. See Li et al. (1992) *Cell* 69:915–926. Resulting ES cell lines were genotyped by PCR and two null lines were obtained from twenty embryo cultures. Briefly, PCR analysis of DNA from ES cells generated from blastocysts of a FN/129 heterozygous x heterozygous mating demonstrate a 900 bp product from the wild-type allele, and a 1060 bp product from the targeted allele.

Derivation of Fibronectin-/-Fibroblasts

Fibronectin (FN)-null mouse fibroblasts were derived from the fibronectin-null ES cells. The ES cells were differentiated into a mixed population by culture in 1.0% DMSO. The cultures were enriched for cells with a fibroblastic morphology by several passages with trypsinization. Cells were then immortalized by infection with a recombinant retrovirus that transduced SV40 large T antigen (as described in Fassler et al. (1995) *J. Cell. Biol.* 128:979–988) and cloned by limiting dilution. Clones were analyzed by immunofluorescence and flow cytometry, as described in Sakai et al., (1998) *J. Cell. Biol.* 141:527–538, and selected on the basis of ability to deposit exogenous fibronectin into fibrillar extracellular matrix and strong surface expression of $\alpha 5$ and $\beta 1$ subunits of an integrin fibronectin receptor. These cells did not incorporate radiolabeled amino acids into secreted fibronectin (data not shown). There was no detectable staining for extracellular or intracellular fibronectin unless exogenous fibronectin was added.

FN+/-fibroblasts deposited a fibronectin matrix with or without the addition to the culture medium of 10 micrograms/ml fibronectin, whereas FN-/-cells deposited fibronectin into a fibrillar matrix only if fibronectin was added to the medium. Transcription of the syndecan-4 core protein gene by FN-/-cells was demonstrated by RT-PCR analysis of one $\mu$g of total RNA prepared from $10^7$ FN-/-or 3T3 fibroblasts cultured on fibronectin. PCR reactions were performed with primers specific for syndecan-4 (forward: NT +76 to +100 and reverse: NT +443 to +464) resulting in the amplification of a 388 bp DNA fragment. For control of specificity, $H_2O$ or RNA without reverse transcription into cDNA was added to the PCR reactions instead of cDNA from FN-/-or 3T3 fibroblasts. The FN-/-cells express the core protein of syndecan-4 on their cell surfaces as indicated from the flow cytometric analysis.

Cell Culture

For the experiments reported here, FN-/-fibroblasts (clone 5F) were maintained at subconfluent densities in DMEM supplemented with 10% fetal bovine serum (FBS), streptomycin (250 $\mu$g/ml) and penicillin (250 units/ml)(Life Technologies, Gaithersburg, Md.) in a humidified atmosphere of 10% $CO_2$, at 37° C. The cells were rinsed with DMEM without FBS, trypsinized and plated on coverslips that had been coated for 2 hours at room temperature with 50 $\mu$l of a solution of fibronectin (200 $\mu$g/ml; Collaborative Medical Products; Bedford, Mass.), the 120 kDa $\alpha$-chymotryptic cell binding domain of fibronectin (200 $\mu$g/ml) (Life Technologies, Gaithersburg, Md.), polylysine (100 $\mu$g/ml)(Sigma, St. Louis, Mo.), or a rat monoclonal antibody directed against the mouse $\beta 1$ integrin chain (200 $\mu$g/ml) (PharMingen, San Diego, Calif.). FN-/-fibroblasts were allowed to attach to the substrate for 2 hours and maintained for an additional 2 to 4 hours during which they were supplemented with 50 $\mu$l of either affinity-purified antibodies directed against the ectodomain of mouse syndecan-4 (0.175 $\mu$g/ml), the 40 kDa $\alpha$-chymotryptic heparin-binding domain of fibronectin (0.2 $\mu$g/ml) (Chemicon International, Temecula, Calif.), C3 exotransferase (15 $\mu$g/ml) (List Biological Laboratories Inc., Campbell, Calif.) or lysophosphatidic acid (500 ng/ml;). Cells were fixed in 4% paraformaldehyde and examined for focal adhesions and stress fibers.

PCR analysis of FN−/−and 3T3 fibroblasts demonstrated a 388 bp band which indicates the presence of mRNA for syndecan-4 in 3T3, and FN−/−fibroblasts. No band is visible in PCR reactions where the cDNA is replaced by non-reverse-transcribed RNA from FN−/−cells or $H_2O$.

Antibody Production

Rabbit polyclonal antibodies were directed against a unique amino acid sequence of the ectodomain of mouse syndecan-4. The immunogen was a synthetic peptide whose sequence was deduced from a mouse syndecan-4 cDNA clone. The sequence ($I^{90}$ to $G^{122}$) deduced from the clone used in these experiments differed from the murine syndecan-4 sequence as described in Tsuzuki et al. (1997) *J: Biochem*. 122:17–24, at amino acid residue 117, where alanine$^{117}$ was replaced with a valine$^{117}$. For the immunization protocol, 3.5 mg of peptide were mixed with 0.75 mg of methylated bovine serum albumin in 1.0 ml of phosphate-buffered saline (PBS) and mixed with the RIB1 R-730 adjuvant before immunization as described in Benoit et al. (1982) *Prot. Natl. Acad. Sci USA* 79:917–921. This antibody was referred to as MS-4-E. Antibodies (immune and preimmune) were affinity-purified on a protein-G column (Pierce, Rockford, Ill.) according to the manufacturer's recommendations. The specificity of the anti-mouse syndecan-4 antibodies was evaluated by Western blot analysis after SDS-PAGE of 1.8 mg each of purified mouse syndecan-4 ectodomain (amino acids 24–144) and full length chicken syndecan-4 core protein (Baciu et al. (1994) *J. Biol. Chem*. 269:696–703) expressed as maltose-binding fusion proteins in bacteria. After electrophoresis, the proteins were transferred to an Immobilon-P membrane (Millipore Corporation, Bedford, Mass.), blocked with 5% non-fat dry milk in PBS, 0.2% Tween 20 and incubated with a 1:300 dilution of purified rabbit IgG or anti-mouse syndecan-4 antibodies (MS-4-E) or a 1:3,000 dilution of purified antibodies directed against the ectodomain of chicken syndecan-4 core protein (CS-4-E; 23). The bound antibodies were detected with a horseradish-conjugated secondary antibody and the ECL reagents (Renaissance, NEN, Boston, Mass.) according to the manufacturer's protocol.

A shift in fluorescence intensity is evident with the anti-mouse syndecan-4 antibody and the anti-β1 integrin chain antibody but not with the secondary antibodies. The specificity of the anti-mouse syndecan-4 antibodies is indicated from tests in which bacterially expressed mouse syndecan4 ectodomain fusion protein is recognized by the anti-mouse syndecan-4 antibody (MS-4-E), but not by an anti-chicken syndecan-4 antibody (CS-4-E) and the bacterially expressed chicken syndecan-4 core protein fusion protein is recognized by the anti-chicken syndecan-4 antibody, but not by the anti-mouse syndecan-4 antibody.

Flow Cytometry

Surface expression of syndecan-4 on FN−/−fibroblasts was analyzed by flow cytometry (FACScan; Becton Dickinson, San Jose, Calif.) as described in Echtermeyer et al. (1998) *J. Biol. Chem*. 271:2071–2075. Briefly, $2×10^5$ cells, released from fibronectin-coated culture dishes in ice-cold PBS, were incubated for 60 minutes at 4° C. with a 1:10 dilution of the affinity-purified anti-mouse syndecan-4 antibody (MS-4-E) or a 1:100 dilution of a rat monoclonal antibody directed against the mouse β1 integrin chain (9EG7) in the presence of propidium. After washing with PBS containing 5% fetal calf serum, the cells were stained with a 1:200 dilution of fluorescein isothiocyanate-conjugated goat anti-rabbbit or goat anti-rat antibodies (Santa Cruz Biotechnology, Inc., Santa Cruz, Calif.). Fluorescence intensity was measured within 1 hour.

Damaged cells that had incorporated propidium iodide were excluded from the fluorescence measurements. Surface expression of syndecan-4 and β1 integrins analyzed by flow cytometry after staining with affinity-purified rabbit antibody against mouse syndecan-4 or with a rat monoclonal antibody against mouse β1 integrin.

Immunocytochemistry

After fixation the cells were stained for vinculin or actin. The vinculin monoclonal antibody (hVin-1, Sigma, St. Louis, Mo.) was used at a 1:400 dilution. To visualize the primary antibody staining, the slides were incubated with a 1:100 dilution of FITC-conjugated anti-mouse antibodies (Jackson ImmunoResearch Laboratories, Inc., West Grove, Pa.) for 45 minutes at 37° C. TRITC-phalloidin (Molecular Probes, Eugene, Oreg.) was used for actin staining according to the manufacturer's instructions. Immunocytochemical analysis was carried out with a Leica confocal microscope. Of the emission channels used during double labeling experiments, excitation levels and gain were set to eliminate bleed-through from one channel to the other as outlined by the manufacturer. This was verified experimentally. Non-specific staining was determined by use of secondary antibody alone.

The following results demonstrate the assembly of focal adhesions and actin stress fibers in FN−/−cells plated on fibronectin. FN−/−fibroblasts attach when plated on fibronectin, and 98% of the attached cells are fully spread (See Table 1). In addition, FN−/−fibroblasts plated on fibronectin formed focal adhesions and establish an elaborate actin cytoskeleton. In contrast, when FN−/−cells were plated on the 120 kDa cell-binding domain (CBD) of fibronectin, 94% of the cells maintain a round morphology without organized focal adhesions and stress fibers. The 6% of the FN−/−cells plated on the CBD that were spread formed focal adhesions and a cytoskeleton, although both types of structures were less developed than those seen in cells plated on full length fibronectin. When cells plated on the 120 kDa CBD of fibronectin were supplemented with the 40 kDa heparin-binding domain in solution, 47% of the attached cells spread and developed focal adhesions and an actin cytoskeleton. The extent of spreading with this treatment was not as pronounced as that seen when cells are plated on intact fibronectin. These results are in agreement with those reported by Woods et al. (1986) *EMBO J*. 5:665–670.

A very striking change in morphology was seen when FN−/−fibroblasts plated on the 120 kDa CBD of fibronectin were supplemented with medium containing antibodies directed against the ectodomain of mouse syndecan-4. In this case, 90% of the attached cells spread and formed focal adhesions and an elaborate actin cytoskeleton. These cells spread to the same extent as those plated on full length fibronectin. No such changes were evident when the cells were treated with the same concentration of pre-immune antibodies instead of the anti-syndecan-4 antibodies. Similarly, when antibodies directed against mouse β1 integrin chains were used as substrate instead of the cell-binding domain of fibronectin, 85% of the attached FN−/−cells were fully spread and assembled focal adhesions and actin stress fibers in the presence of anti-mouse syndecan-4 antibodies. In the presence of the same concentration of pre-immune antibodies, 94% of the cells remained round without an organized cytoskeleton. In contrast, when FN−/−fibroblasts were plated on polylysine, they spread somewhat but 95% of the cells did not assemble focal adhesions or an actin cytoskeleton in the presence of either anti-syndecan-4 antibodies or IgG. The staining pattern of vinculin is diffuse and the actin has a cortical distribution in these cells.

Thus, the anti-syndecan4 antibodies can substitute for the heparin-binding domain of fibronectin for full spreading and assembly of focal adhesions and actin stress fibers in cells plated on either the cell-binding domain of fibronectin or on anti-mouse β1 integrin chain antibodies, but not in cells plated on polylysine. Thus, the occupancy of both syndecan-4 and integrins is necessary for full cell spreading and assembly of focal adhesions and actin stress fibers.

The Cytoskeletal Reorganization Regulation by Rho.

The small GTP-binding protein Rho is a key regulator of focal adhesion and stress fiber formation for signaling events through integrins. See Clark et al. (1998) *J. Cell. Biol.* 142:573–586. To test if the activity of Rho is also required for the effects of anti-syndecan-4 antibodies, FN−/−fibroblasts were allowed to attach to the 120 kDa cell-binding domain (CBD) of fibronectin for two hours. During the next two hours, half of the cells remained unsupplemented and half were supplemented with *Clostridium botulinum* C3 exotransferase, which ADP-ribosylates and inactivates Rho. During the last two hours, half of each group was supplemented with the affinity-purified anti-mouse syndecan-4 antibodies. In the group that did not receive C3 exotransferase and was not supplemented with the anti-syndecan-4 antibody, 94% of the attached cells remained round (Table 1) and did not assemble focal adhesions or actin stress fibers. In addition, these cells did not spread with the addition C3 actin stress fibers in 92% of the cells examined. Only 8% of the cells that adhered to the 120 kDa CBD of fibronectin had a spread morphology (Table 1). In the group of cells that were treated with C3 exotransferase but no anti-syndecan 4 antibody, 6% of the adherent cells had a spread morphology (data not shown). Thus, the C3 exotransferase treatment blocks the assembly of focal adhesions and stress fibers that can be induced by anti-syndecan-4 antibodies in cells plated on the CBD of fibronectin. Finally, the addition of lysophosphatidic acid (LPA), which signals through Rho, to cells plated on the 120 kDa CBD of fibronectin leads to full spreading and extensive focal adhesion and actin stress fiber assembly in 95% of the attached cells. Therefore, focal adhesions and stress fibers in cells adherent to the CBD of fibronectin can be induced either by LPA, known to activate Rho, or by antibodies to syndecan-4, in a Rho-dependent fashion. The simplest implication of these results is that Rho-mediated regulation of focal adhesion and stress fiber assembly in cells plated on fibronectin results from cooperative signaling through integrins and syndecan-4.

TABLE 1

Summary of morphology of FN-/-fibroblasts cultured under various conditions.

| Substrate | Supplemental | % of attached cells that assemble focal adhesions and actin stress fibers | Corresponding Figures |
|---|---|---|---|
| FN | None | 98 | 4A |
| 120 kDa | None | 6 | 4B |
|  | 40 kDa | 47 | 4C |

TABLE 1-continued

Summary of morphology of FN-/-fibroblasts cultured under various conditions.

| Substrate | Supplemental | % of attached cells that assemble focal adhesions and actin stress fibers | Corresponding Figures |
|---|---|---|---|
|  | Anti-syndecan-4-antibodies | 90 | 4D |
|  | IgG | 5 | 4E |
| Anti-β1 mAb | None | 4 |  |
|  | Anti-syndecan-4-antibodies | 85 | 4F |
|  | IgG | 6 | 4G |
| Polylysine | None | 5 |  |
|  | Anti-syndecan-4-antibodies | 6 | 4H |
|  | IgG | 5 | 4I |
| 120 kDa | None | 6 | 5A |
|  | Anti-syndecan-4-antibodies | 89 | 5B |
|  | Anti-syndecan-4-antibodies + C3 | 8 | 5C |
|  | LPA | 95 | 5D |

A minimum of 50 cells were counted for each experiment. FN=Fibronectin; 120 kDa=120 kDa α-chymotryptic cell-binding domain of fibronectin; Anti-p1 mAb=rat monoclonal antibody directed against mouse β1 integrin chain; 40 kDa=40 kDa α-chymotryptic heparin-binding domain of fibronectin; Anti-syndecan-4 antibodies=the antibodies are directed against the ectodomain of mouse syndecan-4 core protein; C3=C3 exotransferase; LPA=Lysophosphatidic acid.

Analogs of Syndecan-4 or the Heprin Binding Domain of Fibronectin

Analogs can differ from a naturally-occurring protein in amino acid sequence or in ways that do not involve sequence, or both. Non-sequence modifications include in vivo or in vitro chemical derivatization of the protein. Non-sequence modifications include changes in acetylation, methylation, phosphorylation, carboxylation, or glycosylation.

Preferred analogs include soluble syndecan-4 (or biologically active fragments thereof such as the heparin binding domain-binding portion of syndecan-4) whose sequences differ from the wild-type sequence by one or more conservative amino acid substitutions or by one or more non-conservative amino acid substitutions, deletions, or insertions which do not abolish a syndecan-4 biological activity, e.g., do not abolish the binding of syndecan-4 to the HBD of an ECM molecule. Other preferred analogs include fibronectin, vitronectin, laminins and collagens comprising the heparin binding domain whose sequence differs from wild type sequence by one or more conservative amino acid substitutions or by one or more non-conservative amino acid modifications which do not abolish binding to syndecan-4. Preferably, such fibronectin analogs retain the ability to bind to syndecan-4 but block the generation of adhesion-mediated signaling. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

Production of Fragments and Analogs
Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Generation of Analogs: Production of Altered DNA and Peptide Sequences by Random Methods Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Generation of Analogs: Production of Altered DNA and Peptide Sequences by Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci.* USA, 75: 5765[1978]).

Cassette Mutagenesis

Another method for preparing variants, cassette mutagenesis, is based on the technique described by Wells et al. (*Gene*, 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. For example, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to other syndesmos subunits, assembly into a trimeric syndesmos molecules, binding to natural ligands or substrates, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid (interaction trap) assays such as the system described above (as with the other screening methods described herein), can be used to identify fragments or analogs (see e.g., U.S. Pat. No. : 5,283,317; PCT publication WO94/10300; Zervos et al. (1993) *Cell* 72:223–232; Madura et al. (1993) *J. Biol Chem* 268:12046–12054; Bartel et al. (1993) *Biotechniques* 14:920–924; and Iwabuchi et al. (1993) *Oncogene* 8:1693–1696). These may include agonists, superagonists, and antagonists. (The subject protein and a protein it interacts with are used as the bait protein and fish proteins.). These assays rely on detecting the reconstitution of a functional transcriptional activator mediated by protein-protein interactions with a bait protein. In particular, these assays make use of chimeric genes which express hybrid proteins. The first hybrid comprises a DNA-binding domain fused to the bait protein. e.g., a syndecan-4 molecule or a fragment thereof. The second hybrid protein contains a transcriptional activation domain fused to a "fish" protein, e.g. an expression library, e.g., an embryonic limb bud expression library. If the fish and bait proteins are able to interact, they bring into close proximity the DNA-binding and transcriptional activator domains. This proximity is sufficient to cause transcription of a reporter gene which is operably linked to a transcriptional regulatory site which is recognized by the DNA binding domain, and expression of the marker gene can be detected and used to score for the interaction of the bait protein with another protein.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the NH2-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J.* 12:725–734; Clackson et al. (1991) *Nature* 352:624–628; and Barbas et al. (1992) *PNAS* 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce tides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) *Bio/Tech.* 6, 1080–1083). Surface proteins of other bacterial species have also served as peptide fusion partners. Examples include the Staphylococcus protein A and the outer membrane protease IgA of Neisseria (Hansson et al: (1992) *J. Bacteriol.* 174, 4239–4245 and Klauser et al. (1990) *EMBO J.* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. USA*. 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. USA*. 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupe to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204,357–364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of interest is identified, it is routine to perform for one skilled in the art to obtain analogs and fragments.

Peptide Mimetics

The invention also provides for reduction of the protein binding domains of the subject syndecan-4 polypeptides or fibronectin (e.g., the HBD) to generate mimetics, e.g. peptide or non-peptide agents. See, for example, "Peptide inhibitors of human papillomavirus protein binding to retinoblastoma gene protein" European patent applications EP-412,762A and EP-B31,080A.

Non-hydrolyzable peptide analogs of critical residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), ketomethylene pseudopeptides (Ewenson et al. (1986) *J. Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al.,(1985) *Tetrahedron Lett* 26:647; and Sato et al. (1986) *J. Chem Soc Perkin Trans* 1:1231 and β-aminoalcohols (Gordon et al. (1985) *Biochem Biophys Res Commun*126:419; and Dann et al. (1986) *Biochem Biophys Res Commun* 134:71).

Antibodies

The invention also includes antibodies specifically reactive with a subject syndecan-4 polypeptides, e.g., the ectodomain of syndecan-4. Anti-protein/anti-peptide antisera or monoclonal antibodies can be made as described herein by using standard protocols (See, for example, *Antibodies: A Laboratory Manual* ed. by Harlow and Lane (Cold Spring Harbor Press: 1988)).

Another application of antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a subject polypeptide can then be detected with antibodies, as, for example, reacting nitrocellulose filters lifted from infected plates with antibodies of the invention. Phage, scored by this assay, can then be isolated from the infected plate. Thus, the presence of homologs can be detected and cloned from other animals, and alternate isoforms (including splicing variants) can be detected and cloned from human sources.

Chimeric and Humanized Antibodies.

Recombinant forms of antibodies, such as chimeric and humanized antibodies, can also be prepared to minimize the response by a human host to a antibody, e.g., an anti-syndecan4 antibody. When antibodies produced in non-human subjects or derived from expression of non-human antibody genes are used therapeutically in humans, they are recognized to varying degrees as foreign and an immune response may be generated in the recipient. One approach for minimizing or eliminating this problem is to produce chimeric antibody derivatives, i.e., antibody molecules that combine a non-human animal variable region and a human constant region. Such antibodies retain the epitope binding specificity of the original monoclonal antibody, but may be less immunogenic when administered to humans, and therefore more likely to be tolerated by the patient.

Chimeric monoclonal antibodies can be produced by recombinant DNA techniques known in the art. For example, a gene encoding the constant region of a non-human antibody molecule is substituted with a gene encoding a human constant region. (see Robinson et al., PCT Patent Publication PCT/US86/02269; Akira, et al., European Patent Application 184,187; Taniguchi, M., European Patent Application 171,496; Morrison et al., European Patent Application 173,494; Neuberger et al., PCT Application WO 86/01533; Cabilly et al. U.S. Pat. No. 4,816,567; Cabilly et al., European Patent Application 125,023; Better et al. (1988 *Science* 240:1041–1043); Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl Cancer Inst.* 80:1553–1559).

A chimeric antibody can be further "humanized" by replacing portions of the variable region not involved in antigen binding with equivalent portions from human variable regions. General reviews of "humanized" chimeric antibodies are provided by Morrison, S. L. (1985) *Science* 229:1202–1207 and by Oi et al. (1986) *BioTechniques* 4:214. Such methods include isolating, manipulating, and expressing the nucleic acid sequences that encode all or part of an immunoglobulin variable region from at least one of a heavy light chain. The cDNA encoding the humanized chimeric antibody, or fragment thereof, can then be cloned into an appropriate expression vector. Suitable "humanized" antibodies can be alternatively produced by CDR or CEA substitution (see U.S. Pat. No. 5,225,539 to Winter; Jones et al. (1986) *Nature* 321:552–525; Verhoeyan et al. (1988) *Science* 239:1534; and Beidler et al. (1988) *J. Immunol.* 141:4053–4060).

Epitope imprinting can also be used to produce a "human" antibody polypeptide dimer which retains the binding specificity of a murine antibody specific for an antigen. Briefly, a gene encoding a non-human variable region (VH) with binding specificity to an antigen and a human constant region (CH1) is expressed in *E. coli* and infected with a phage library of human VλCλ genes. Phage displaying antibody fragments are subject to panning with the antigen. Selected human Vλ genes are recloned for expression of VλCλ chains and *E. coli* harboring these chains are infected with a phage library of human VHCH1 genes and the library is subject to rounds of panning with antigen coated tubes. See Hoogenboom et al. PCT publication WO 93/06213.

Fusion Proteins

Polypeptides for use in modulating cell attachment and/or spreading can be fused to another protein or portion thereof. For example, a syndecan-4 protein or portion thereof, such as the HBD-binding portion of syndecan-4, can be operably linked to another polypeptide moiety to enhance solubility. Examples of a protein which can be fused with syndecan-4 or portions thereof include a plasma protein or fragment thereof, which can improve the circulating half life of syndecan-4. For example, the fusion protein can be a syndecan-4-immunoglobulin (Ig) fusion protein in which the syndecan-4 sequence is fused to a sequence derived from the immunoglobulin superfamily. Several soluble fusion protein constructs have been disclosed wherein the extracellular domain of a cell surface glycoprotein is fused with the constant F(c) region of an immunoglobulin. For example, Capon et al. (1989) *Nature* 337(9):525–53 1, provide guidance on generating a longer lasting CD4 analog by fusing CD4 to an immunoglobulin (IgG1). See also, Capon et al., U.S. Pat. Nos. 5,116,964 and 5,428,130 (CD4-IgG fusion constructs); Linsley et al., U,S, Pat. No. 5,434, 131 (CTLA4-IgG1 and B7-IgG1 fusion constructs); Linsley et al. (1991) *J. Exp. Med* 174:561–569 (CTLA4-IgG1 fusion constructs); and Linsley et al. (1991) *J. Exp. Med* 173:721–730 (CD28-IgG1 and B7-IgG1 fusion constructs). Such fusion proteins have proven useful for modulating receptor-ligand interactions and reducing inflammation in vivo. For example, fusion proteins in which an extracellular domain of cell surface tumor necrosis factor receptor (TNFR) proteins has been fused to an immunoglobulin constant (Fc) region have been used in vivo. See, for example, Moreland et al. (1997) *N. Engl. J. Med.* 337(3) :141–147; and, van der Poll et al. (1997) *Blood* 89(10) :3727–3734).

Pharmaceutical Compositions

The polypeptides, nucleic acid molecules and antibodies of the invention can be incorporated into pharmaceutical compositions suitable for administration. Such compositions typically comprise the protein, nucleic acid molecule, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition can be formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solve it or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterlization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any addition desired ingredient from a previously sterile-filtered solution thereof.

The active compounds can be prepared with carriers that will protect the compound against rapid elimination from the body, such as a controlled release formation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) *Proc. Natl. Acad. Sci. USA* 91:3054–3057). The pharmaceuitical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

Other embodiments are with the following claims.

What is claimed:

1. A method of modulating one or more of cell attachment, cell spreading, cell migration, or formation or dissolution of a focal adhesion, comprising: administering an antibody that binds to a syndecan-4 ectodomain on a cell surface and modulates the interaction between the syndecan-4 ectodomain and a heparin binding domain (HBD) of an extracellular matrix molecule, thereby modulating said one or more of cell attachment, cell spreading, cell migration, or formation or dissolution of focal adhesion.

2. The method of claim 1, further comprising administering an anti-integrin antibody that modulates integrin binding.

3. The method of claim 1, further comprising administering a polypeptide comprising a cell binding domain (CBD) of fibronectin that modulates integrin binding.

4. A method of modulating one or more of cell attachment, cell spreading, cell migration, or formation or dissolution of a focal adhesion, comprising: administering a soluble syndecan-4 ectodomain polypeptide that binds to a heparin binding domain (HBD) of an extracellular matrix molecule, and modulates the interaction between the syndecan-4 ectodomain and the HBD of an extracellular matrix molecule, thereby modulating said one or more of cell attachment, cell spreading, cell migration, or formation or dissolution of focal adhesion.

5. The method of claim 4, wherein the polypeptide comprises from about amino acids 90 to 120 of SEQ ID NO: 2.

6. The method of claim 4, further comprising administering an anti-integrin antibody that modulates integrin binding.

7. The method of claim 4, further comprising administering a polypeptide comprising a cell binding domain (CBD) of fibronectin that modulates integrin binding.

* * * * *